(12) United States Patent
Reddy et al.

(10) Patent No.: US 8,541,580 B2
(45) Date of Patent: Sep. 24, 2013

(54) PROCESS FOR THE PREPARATION OF PYRAZINONE THROMBIN INHIBITOR AND ITS INTERMEDIATES

(75) Inventors: Reguri Buchi Reddy, Morris Plains, NJ (US); Upparapalli Sampathkumar, Morris Plains, NJ (US); Nilam Sahu, Morris Plains, NJ (US); Jawaji Karunakara Rao, Morris Plains, NJ (US); Gade Brahma Reddy, Morris Plains, NJ (US)

(73) Assignee: Diakron Pharmaceuticals, Inc., Morris Plains, NJ (US)

( * ) Notice: Subject to any disclaimer, the term of this patent is extended or adjusted under 35 U.S.C. 154(b) by 247 days.

(21) Appl. No.: 12/938,297

(22) Filed: Nov. 2, 2010

(65) Prior Publication Data
US 2011/0105753 A1 May 5, 2011

(30) Foreign Application Priority Data
Nov. 3, 2009 (IN) .......................... 2663/CHE/2009

(51) Int. Cl.
*C07D 401/14* (2006.01)
(52) U.S. Cl.
USPC .......................................................... 544/405
(58) Field of Classification Search
USPC .......................................................... 544/405
See application file for complete search history.

(56) References Cited

U.S. PATENT DOCUMENTS

| 6,147,078 A | 11/2000 | Sanderson et al. |
| 6,455,532 B1 | 9/2002 | Burgey et al. |
| 7,456,290 B2 | 11/2008 | Vangelisti et al. |

FOREIGN PATENT DOCUMENTS

| EP | 1 422 221 A1 | 5/2004 |
| WO | WO 02/46160 A2 | 6/2002 |

OTHER PUBLICATIONS

Wade, Jr., L.G., "Reactions of Alcohols," *Organic Chemistry*, 5th Edition, Chapter 11, PowerPoint Presentation, Dallas County Community College District, Slides 12-15 (2003); faculty.smu.edu/ebiehl/organic/Wade11.ppt.
International Search Report and Written Opinion issued in corresponding PCT Application No. PCT/US10/55176, mailed Jan. 18, 2011.
Ashwood et al., "Development of a Scaleable Synthesis of a 3-Aminopyrazinone Acetamide Thrombin Inhibitor", *Organic Proc. Res. Dev.* 8(2):192-200, 2004.
Supplementary Search Report in corresponding European Patent Application No. 10828989.3 dated May 23, 2013.
Friedrich et al., "Titanium and Zirconium Complexes Containing a Novel Dianionic Trifunctional Amido Ligand," Chem. Ber./Recueil 1997, vol. 130, pp. 1751-1759.
Burgey et al., "Metabolism-Directed Optimization of 3-Aminopyrazinone Acetamide Thrombin Inhibitors. Development of an Orally Bioavailable Series Containing P1 and P3 Pyridines," J. Med. Chem., 2003, vol. 46, pp. 461-473.

*Primary Examiner* — Brian McDowell
(74) *Attorney, Agent, or Firm* — Knobbe Martens Olson & Bear LLP

(57) ABSTRACT

Improved process for the preparation of 3-fluoro-2-pyridyl-methyl-3-(2,2-difluoro-2-(2-pyridyl)ethylamino)-6-chloro-pyrazin-2-one-1-acetamide of formula (I) and its intermediates is provided.

(I)

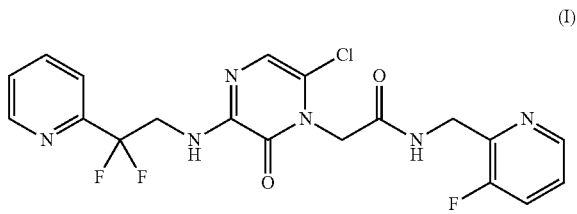

13 Claims, No Drawings

PROCESS FOR THE PREPARATION OF PYRAZINONE THROMBIN INHIBITOR AND ITS INTERMEDIATES

RELATED APPLICATION

This application claims priority under 35 U.S.C. §119(a)-(d) to Indian Provisional Patent Application No. 2663/CHE/2009, filed Nov. 3, 2009, the entire contents of which are incorporated herein by reference.

FIELD OF THE INVENTION

Processes for the preparation of 3-fluoro-2-pyridylmethyl-3-(2,2-difluoro-2-(2-pyridyl)ethylamino)-6-chloropyrazin-2-one-1-acetamide of the formula (I) and its intermediates are described.

(I)

BACKGROUND OF THE INVENTION

3-Fluoro-2-pyridylmethyl-3-(2,2-difluoro-2-(2-pyridyl)ethylamino)-6-chloro pyrazin-2-one-1-acetamide of formula (I), which is useful as thrombin inhibitor is described in U.S. Pat. No. 6,455,532 B1. The following scheme-A is provided in U.S. Pat. No. 6,455,532 B1 for the preparation of compound of formula (I).

Scheme -A

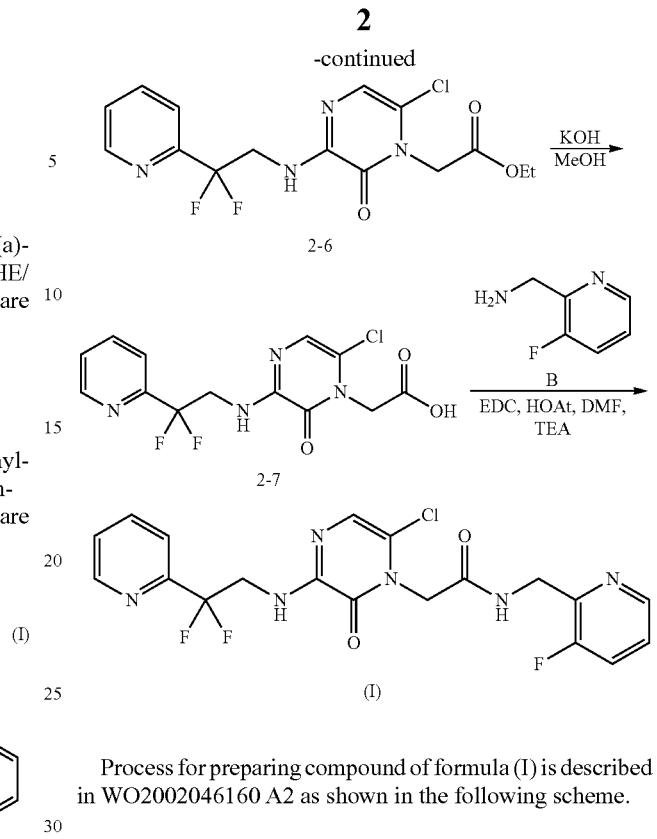

Process for preparing compound of formula (I) is described in WO2002046160 A2 as shown in the following scheme.

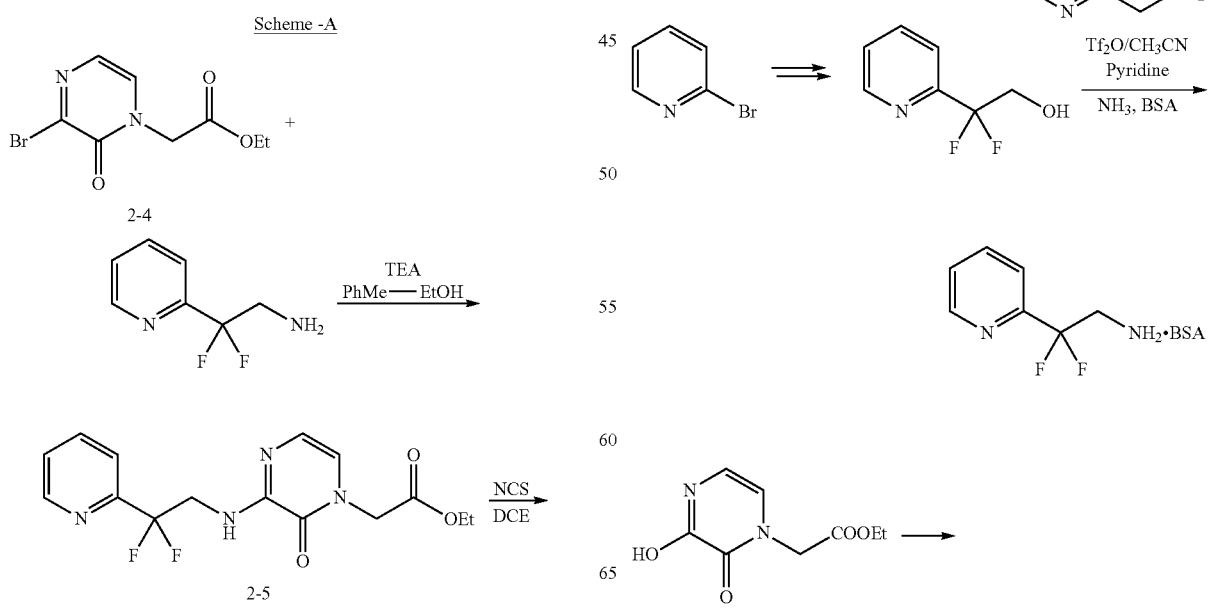

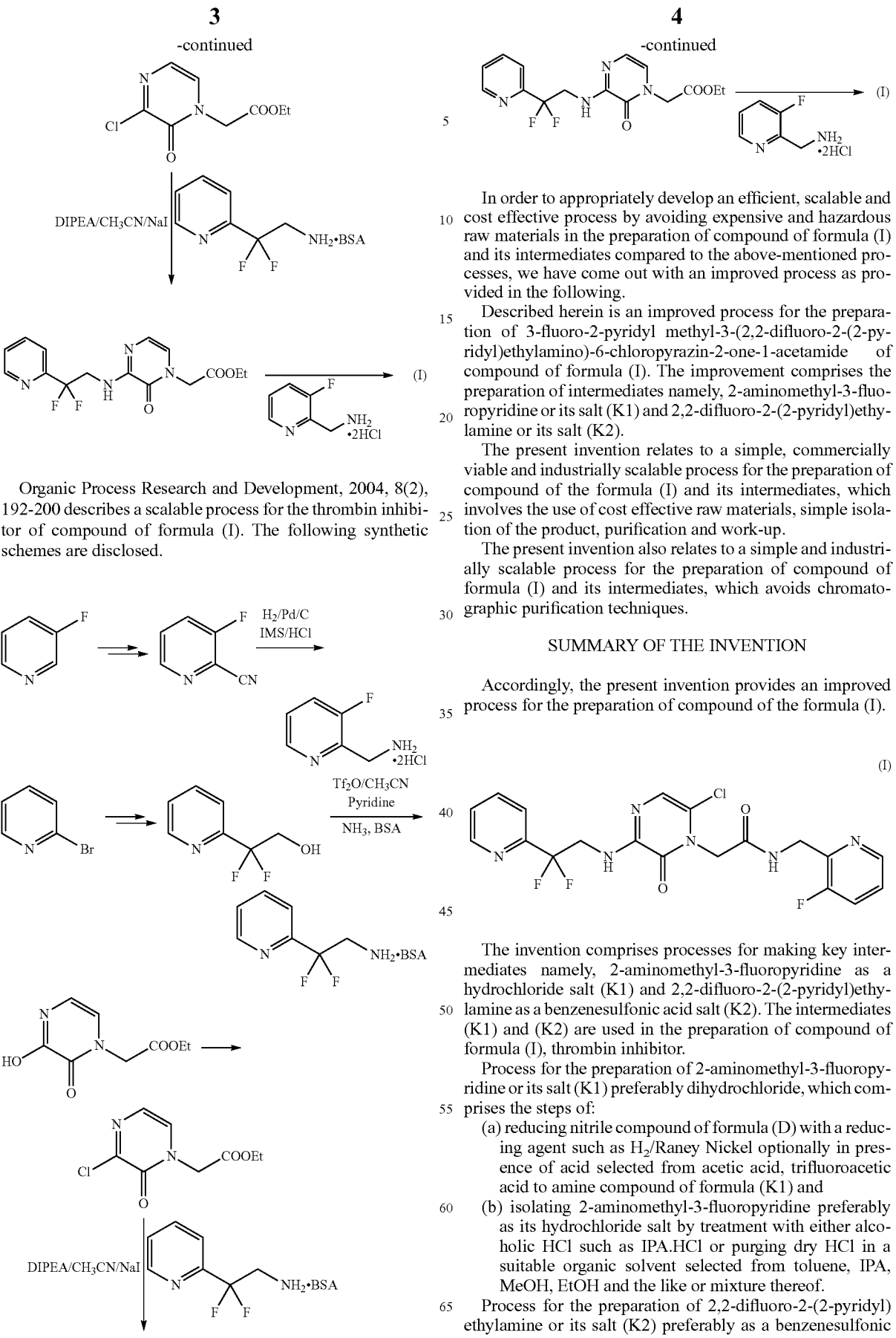

Organic Process Research and Development, 2004, 8(2), 192-200 describes a scalable process for the thrombin inhibitor of compound of formula (I). The following synthetic schemes are disclosed.

In order to appropriately develop an efficient, scalable and cost effective process by avoiding expensive and hazardous raw materials in the preparation of compound of formula (I) and its intermediates compared to the above-mentioned processes, we have come out with an improved process as provided in the following.

Described herein is an improved process for the preparation of 3-fluoro-2-pyridyl methyl-3-(2,2-difluoro-2-(2-pyridyl)ethylamino)-6-chloropyrazin-2-one-1-acetamide of compound of formula (I). The improvement comprises the preparation of intermediates namely, 2-aminomethyl-3-fluoropyridine or its salt (K1) and 2,2-difluoro-2-(2-pyridyl)ethylamine or its salt (K2).

The present invention relates to a simple, commercially viable and industrially scalable process for the preparation of compound of the formula (I) and its intermediates, which involves the use of cost effective raw materials, simple isolation of the product, purification and work-up.

The present invention also relates to a simple and industrially scalable process for the preparation of compound of formula (I) and its intermediates, which avoids chromatographic purification techniques.

SUMMARY OF THE INVENTION

Accordingly, the present invention provides an improved process for the preparation of compound of the formula (I).

The invention comprises processes for making key intermediates namely, 2-aminomethyl-3-fluoropyridine as a hydrochloride salt (K1) and 2,2-difluoro-2-(2-pyridyl)ethylamine as a benzenesulfonic acid salt (K2). The intermediates (K1) and (K2) are used in the preparation of compound of formula (I), thrombin inhibitor.

Process for the preparation of 2-aminomethyl-3-fluoropyridine or its salt (K1) preferably dihydrochloride, which comprises the steps of:
(a) reducing nitrile compound of formula (D) with a reducing agent such as $H_2$/Raney Nickel optionally in presence of acid selected from acetic acid, trifluoroacetic acid to amine compound of formula (K1) and
(b) isolating 2-aminomethyl-3-fluoropyridine preferably as its hydrochloride salt by treatment with either alcoholic HCl such as IPA.HCl or purging dry HCl in a suitable organic solvent selected from toluene, IPA, MeOH, EtOH and the like or mixture thereof.

Process for the preparation of 2,2-difluoro-2-(2-pyridyl) ethylamine or its salt (K2) preferably as a benzenesulfonic acid salt, which comprises the steps of:

(i) converting difluoro ethanol compound of formula (H) to tosylate compound of formula (J) using tosyl chloride or mesyl chloride and (ii) treating mesylate or tosylate compound of formula (J) with ammonia to yield difluoroamine compound of formula (K2).

Process for the preparation of 3-fluoro-2-pyridylmethyl-3-(2,2-difluoro-2-(2-pyridyl)ethylamino)-6-chloropyrazin-2-one-1-acetamide, which comprises the steps of:

(A) reacting 2,2-difluoro-2-(2-pyridyl)ethylamine or its salt (K2) with 3-chloropyrazin(1H)-2-one-1-acetate (K3) to form ethyl 3-(2,2-difluoro-2-(2-pyridyl)ethylamino)-pyrazin(1H)-2-one-1-acetate (K);

(B) chlorinating the compound of formula (K) and further reacting with 2-aminomethyl-3-fluoropyridine or its salt (K1) to form 3-fluoro-2-pyridylmethyl-3-(2,2-difluoro-2-(2-pyridyl)ethylamino)-6-chloropyrazin-2-one-1-acetamide, the compound of formula (I); and (C) optional purification of compound of formula (I).

The processes described herein can be used for the preparation of compound of formula (I) as a thrombin inhibitor.

DETAILED DESCRIPTION OF THE PREFERRED EMBODIMENT

Processes for the preparation of compound of formula (I) and key intermediates are described herein.

In a first embodiment, a process for the preparation of 2-aminomethyl-3-fluoropyridine as a hydrochloride salt (K1) is provided. In another embodiment, a process for preparing 2-aminomethyl-3-fluoropyridine.2HCl (K1) comprises reduction of 3-fluoropyridine-2-carbonitrile of a compound of formula (D) with the reducing agent $H_2$/Raney Ni in the presence of acetic acid or trifluoroacetic acid. The reported processes use expensive $H_2$/Pd/C that is replaced with cost-effective Raney Nickel. The synthetic scheme for the preparation of 2-aminomethyl-3-fluoropyridine.2HCl is depicted in Scheme 1 as follows.

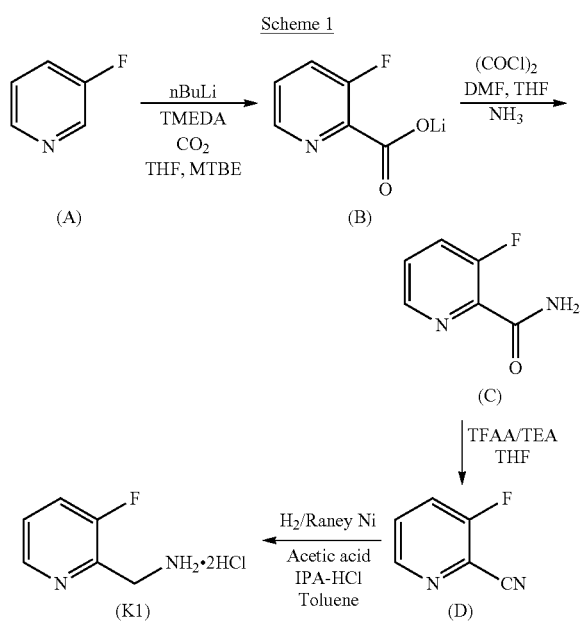

In a second embodiment, a process for the preparation of 2,2-difluoro-2-(2-pyridyl)ethylamine as a benzenesulfonic acid (BSA) salt (K2) is provided (Scheme 2). The improved process utilizes p-toluenesulfonyl chloride (pTsCl or Tosyl chloride) in the preparation of a tosylate or mesylate (J) from the corresponding difluoro alcohol (H). Triflic anhydride $((F_3CSO_2)_2O)$ was used previously in place of low cost pTsCl or MSCl.

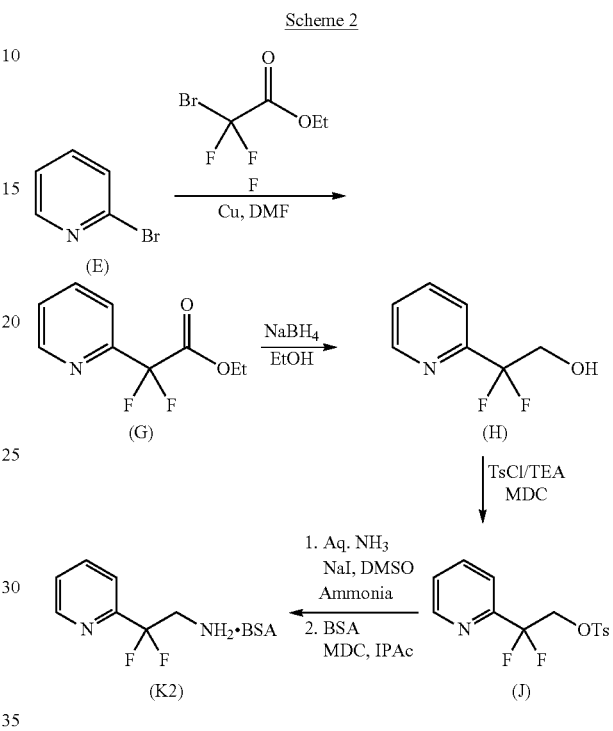

In another embodiment, a process for purifying 3-fluoro-2-pyridylmethyl-3-(2,2-difluoro-2-(2-pyridyl)ethylamino)-6-chloropyrazin-2-one-1-acetamide, a compound of formula (I), using organic solvents including but not limited to ketones, alcohols, esters, ethers, hydrocarbons, halogenated solvents, and the like or a mixture thereof is provided. Ketones include, but are not limited to, acetone, butanone and the like. Alcohols include, but are not limited to, methanol, ethanol, n-propanol, isopropanol (IPA), n-butanol, t-butanol, hexanol, isoamyl alcohol and the like. Esters include, but are not limited to, ethyl acetate, methyl acetate, isopropyl acetate and the like. Ethers include, but are not limited to, diisopropyl ether (IPE), methyl t-butyl ether (MTBE) and the like. Hydrocarbons include, but are not limited to, hexane, heptane, cyclohexane, decalin, pentane and the like. Halogenated solvents include, but not limited to, dichloromethane (MDC), 1,2-dichloroethane and the like or mixture thereof, preferably acetone, isopropyl alcohol or mixtures thereof.

In yet another embodiment a process for the preparation of a compound of formula (I) is provided:

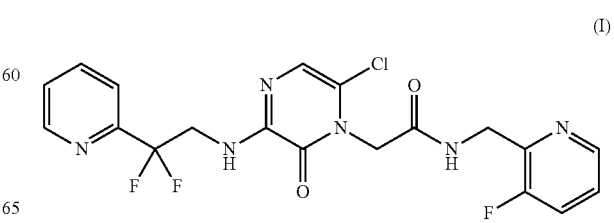

in which 2,2-difluoro-2-(2-pyridyl)ethylamine or its salt (K2) is reacted with ethyl 3-chloropyrazin(1H)-2-one-1-acetate (K3) to form ethyl 3-(2,2-difluoro-2-(2-pyridyl)ethylamino)-pyrazin(1H)-2-one-1-acetate (K), chlorinated, which is further reacted with 2-aminomethyl-3-fluoropyridine or its salt (K1) to form 3-fluoro-2-pyridylmethyl-3-(2,2-difluoro-2-(2-pyridyl)ethylamino)-6-chloropyrazin-2-one-1-acetamide, the compound of formula (I), the improvement comprising:

reducing 2-cyano-3-fluoropyridine with Raney Nickel optionally in the presence of an acid to form 2-aminomethyl-3-fluoropyridine or its salt (K1);

reacting 2,2-difluoro-2-pyridin-2-ylethanol with 4-toluenesulfonyl chloride to form 2,2-difluoro-2-pyridin-2-ylethyl 4-methylbenzenesulfonate, which is converted to compound of formula (K2); and optionally purifying the compound of formula (I).

The term, "salts" used herein includes inorganic acids such as hydrochloride (hydrochloric), hydrobromide (hydrobromic), sulfuric, sulfamic, phosphoric, nitric and the like, or quaternary ammonium salts, which are formed, e.g., from inorganic or organic acids or bases. Examples of acid addition salts include acetate, adipate, alginate, aspartate, benzoate, benzenesulphonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, toluenesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, undecanoate and the like.

Solvates are addition complexes in which a compound is combined with a solvent in some fixed proportion. Solvents include, but are not limited to water, methanol, ethanol, 1-propanol, isopropanol, 1-butanol, isobutanol, t-butanol, acetone, methyl ethyl ketone, acetonitrile, ethyl acetate, benzene, toluene, xylene, ethylene glycol, dichloromethane, 1,2-dichloroethane, N-methylformamide, N,N-dimethylformamide, N-methylacetamide, pyridine, dioxane, diethyl ether and the like. Hydrates are solvates in which the solvent is water. It is to be understood that the definition of the compounds or intermediates of the present invention encompasses all possible hydrates and solvates, in any proportion.

When any term occurs more than once in the patent application, the definition thereof on each occurrence is independent of its definition at every other occurrence. This application contemplates all acceptable acid or base salt forms of the compounds, where applicable.

Thrombin inhibition is used for anticoagulant therapy in individuals having thrombotic conditions, and whenever inhibition of blood coagulation is required such as to prevent coagulation of stored whole blood and to prevent coagulation in other biological samples for testing or storage. Therefore, thrombin inhibitors are added to any medium containing or suspected of containing thrombin and in which it is desired that blood coagulation be inhibited.

The present invention provides an improved process for the preparation of compound of formula (I); an improved process for the preparation of key intermediates of the compound of formula (I); and/or a pharmaceutical composition comprising the compound; and/or a compound for inhibiting thrombin; and/or an improved method for inhibiting thrombin in blood.

The following examples are provided by way of illustration only, which should not be construed to limit the scope of the invention.

Scheme 1

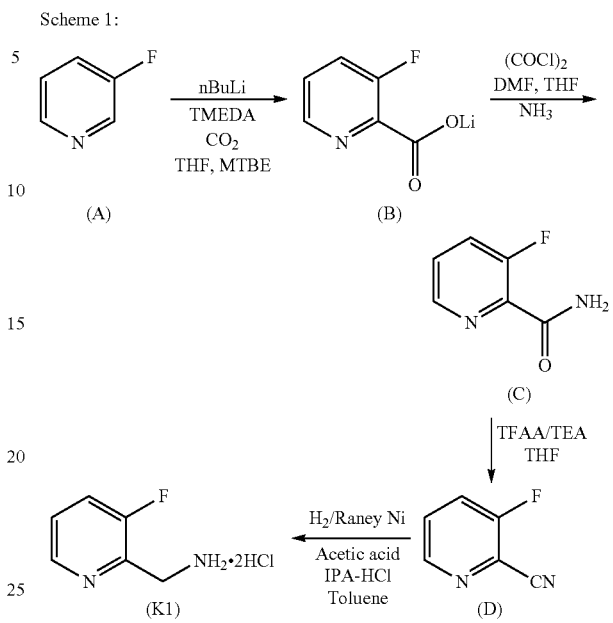

EXAMPLE 1

Preparation of 1-(3-fluoropyridin-2-yl)methanamine dihydrochloride salt (K1)

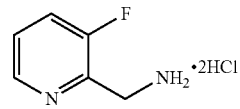

Step-1: Lithium 3-fluoropyridine-2-carboxylate (B)

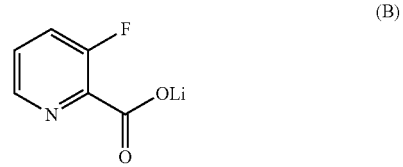

240 mL of Methyl t-butyl ether (MTBE) and 18.55 mL of N,N,N',N'-tetramethylethylenediamine (TMEDA) are taken in a reaction flask under nitrogen atmosphere and cooled to $-70°$ C. to $-60°$ C. To the cooled mass, 80 mL of n-BuLi (1.6 M in hexane) was added dropwise with stirring. Temperature of the reaction mixture (RM) was maintained at $-70°$ C. to $-60°$ C. for 1 hour. The RM was cooled to $-75°$ C., then 10 g of 3-fluoropyridine (in 10 mL of MTBE) was added dropwise while maintaining the temperature in the range of $-75°$ C. to $-70°$ C. The RM was stirred at the same temperature for 4 hours. Meanwhile, in another reaction flask, 100 mL of tetrahydrofuran (THF) was taken and cooled to $-70°$ C. followed by bubbling of $CO_2$ gas for 1 hour. To this solution, lithiated 3-fluoropyridine solution (mixture of 3-fluoropyridine+n-BuLi+TMEDA in MTBE) was added dropwise using cannula maintaining the reaction temperature below −70° C. (−70° C. to −60° C.). Bubbling of CO₂ gas was continued for another hour and then the reaction temperature was slowly brought to +30° C. The resulting solid was filtered, dried and washed with 100 mL of 1:1 THF:MTBE, then vacuum dried at 45° C., resulting in 14.5 g of the titled compound.
Purification The above dried mass (14.5 g) was taken into a reaction flask, 29 mL of methanol was added thereto at room temperature (RT) with stirring, then 145 mL of isopropyl alcohol (IPA) was slowly added. The reaction temperature was maintained at 10° C. to 15° C. for 30 minutes, then the solid obtained was filtered and dried under vacuum, resulting in 12 g of pure Lithium 3-fluoropyridine-2-carboxylate.

Step-2: 3-Fluoropyridine-2-carboxamide (C)

(C)

50 g of Lithium 3-fluoropyridine-2-carboxylate (B), 1.5 mL of N,N-dimethyl formamide (DMF) and 1.15 mL of THF were taken in a reaction flask and cooled to 0-5° C. 74 mL of Oxalyl chloride was added dropwise and the reaction mass was stirred for 2 hours at 0-5° C. After completion of the reaction, ammonia gas was bubbled into the RM for 2 hours and then reaction mass was brought to RT and stirred for 30 minutes. The RM was filtered and washed with 100 mL of THF. The residue was stirred with 300 mL of THF, filtered and washed with 50 mL of THF. The combined filtrates were distilled under vacuum to a residual volume of 100 mL. 450 mL of diisopropyl ether (IPE) was added dropwise to the concentrated mass at RT with stirring. After 30 minutes, the solid obtained was filtered, washed with 100 mL of IPE and dried under vacuum at 40° C. to 45° C. for 8 hours, resulting in 30 g of 3-fluoropyridine-2-carboxamide (C).

Step 3: 3-Fluoropyridine-2-carbonitrile (D)

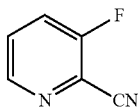

(D)

30 g of 3-Fluoropyridine-2-carboxamide (C), 120 mL of THF and 768.5 mL of TEA were taken in a reaction flask and cooled to 0-5° C. To this mixture, 72.2 mL of Trifluoroacetic anhydride (in 30 mL of THF) was added dropwise over a period of 30 minutes keeping the reaction temperature below 5° C. (0° C. to 5° C.) and the RM was stirred for 2 hours 30 minutes at a temperature below 10° C. (5° C. to 10° C.). After completion of the reaction, 150 mL of 20% Na₂CO₃ solution was added dropwise to the RM while maintaining the temperature below 10° C. (5° C. to 5° C.), followed by addition of 360 mL of purified water. The RM was brought to room temperature (RT) and extracted with dichloromethane (MDC) and the organic layer was washed with 300 mL purified water, 150 mL of 2% dil HCl, followed by purified water and brine. The organic layer was dried over Na₂SO₄ and distilled under vacuum, resulting in the titled compound as a dark brown viscous oily mass. Crude Yield: 22-24 g.

Step 4: 1-(3-Fluoropyridin-2-yl)methanamine dihydrochloride salt (K1)

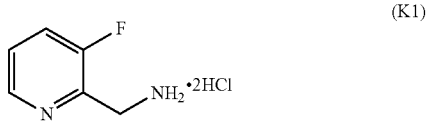

(K1)

3 g of 3-Fluoropyridine-2-carbonitrile (D) (crude), 50 mL of acetic acid and 0.75 g of Raney Ni were taken in a par shaker vessel. The reaction mass was hydrogenated for 4 hours under 6 kg hydrogen pressure at RT. After completion of the reaction, the catalyst was filtered off and the bed was washed with 30 mL of isopropyl alcohol (IPA). The combined filtrate was concentrated under vacuum. To this mass, 30 mL of toluene was added and distilled off to a minimum volume. To the above residue, 20 mL of toluene and 13 mL of IPA.HCl was added dropwise at RT with stirring. After 30 minutes, the RM temperature was brought to 10 to 15° C. and maintained for 30 minutes. The RM was filtered, and the solid was washed with 5 mL of cold IPA, and dried under vacuum at 40° C., resulting in 3.8 g of 1-(3-fluoropyridin-2-yl)methanamine dihydrochloride salt (K1).

Scheme 2

Scheme 2:

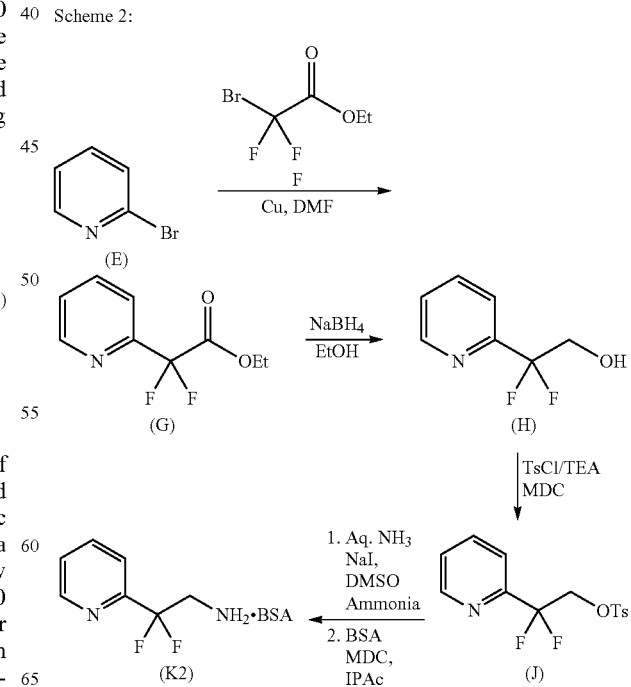

EXAMPLE 2

Preparation of 2,2-Difluoro-2-pyridin-2-ylethanamine benzene sulfonate salt (K2)

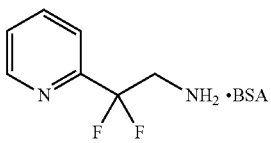
(K2)

Step-1: Preparation of Ethyl difluoro(pyridin-2-yl)acetate (G)

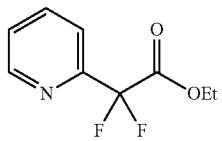
(G)

2-Bromopyridine (20 g), ethyl bromodifluoroacetate (27.2 g) and DMF (120 mL) were added and stirred for 10 minutes under nitrogen. Copper powder was added to the reaction mixture and heated to 70-80° C. for 45 minutes. The reaction mixture was cooled to RT and 400 mL of isopropyl acetate (IPAc) was added. The reaction mixture was quenched with the aqueous potassium dihydrogen phosphate at 0-10° C. and stirred for 30 minutes. The reaction mixture was filtered off and the residue obtained was washed with ethyl acetate. The organic layer was collected and washed with brine solution and dried over sodium sulphate then distilled under vacuum. (Crude weight=20 g).

Step 2: Preparation of 2,2-Difluoro-2-pyridin-2-ylethanol (H)

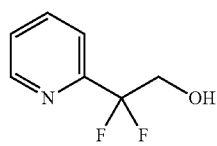
(H)

Ethyl difluoro(pyridin-2-yl)acetate (G) obtained in step 1 (20 g) and 120 mL of ethanol were added, and 4 g of sodium borohydride was added to the reaction mixture over a period of 30 minutes at 0-5° C. The reaction mixture was stirred for 1 hour at 0-10° C. After completion of the reaction, the RM was quenched by adding saturated ammonium chloride solution at 0-5° C. and the volume of reaction mixture was reduced to half by distilling under vacuum. The solution was basified with 50% NaOH solution and extracted with MTBE. The organic layer was washed with a brine solution, dried over sodium sulphate and distilled under vacuum. The crude material was dissolved in 40 mL MTBE, 70 mL of n-hexane at 0-10° C. was added, and the RM was stirred for 30 minutes. The solid obtained was filtered and washed with hexane, resulting in pure product. (Yield=11 g).

Step-3: Preparation of 2,2-Difluoro-2-pyridin-2-ylethyl 4-methylbenzenesulfonate (J)

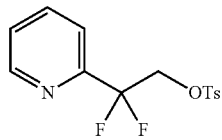
(J)

2,2-Difluoro-2-pyridin-2-ylethanol (H) from step 2 (10 g) was dissolved in 100 mL of MDC, 19 g of TEA was added, then the RM was cooled to 0-10° C. To the cooled solution, 16.77 g of pTsCl was added over a period of 1 hour and stirred for 24 hours at RT. The RM was then quenched with 100 mL of 10% sodium bicarbonate solution and the organic layers were separated. The aqueous layer was extracted with (100 mL×3) MDC. The organic layer was combined and washed with 10% sodium bicarbonate (150 mL), followed by water (150 mL) and a brine solution (150 mL). The organic layer was distilled under vacuum. The crude mass obtained was treated with 30 mL of hexane with cooling and filtered, resulting in pure tosylate. (Weight=15 g, Yield=76.2%). It should be noted that the above process may be followed for the preparation of other sulfonates such as methanesulfonate by using the corresponding sulfonyl chloride (e.g. methanesulfonyl chloride). The compound thus prepared is used in the preparation of a compound of formula (K2). $^1$H-NMR (CDCl$_3$, δ, ppm): 400 MHz: 2.45 (s, 3H), 4.63-4.69 (t, 2H), 7.31-7.33 (d, 2H), 7.36-7.39 (t, 1H), 7.63-7.65 (d, 1H), 7.71-7.73 (d, 2H), 7.79-7.82 (t, 1H), 8.55-8.54 (d, 1H); MS m/z: 314 (M+1).

Step-4: Preparation of 2,2-Difluoro-2-pyridin-2-ylethanamine benzenesulfonate salt (K2)

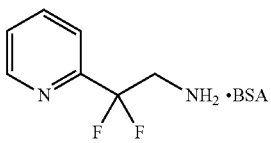
(K2)

10 g of 2,2-Difluoro-2-pyridin-2-ylethyl 4-methylbenzenesulfonate (J) obtained in step 3, 5 g of NaI, 20 mL of DMSO and 90 mL of aqueous ammonia were taken in a 500 mL autoclave vessel. The reaction mixture was heated to 80° C. and a pressure of 15 to 17 kg of ammonia maintained for 30-40 hours. The volume of the reaction mass was reduced by vacuum distillation. The RM was washed with 60 mL of IPE. The pH of the RM was adjusted to 10-14 by adding a 50% NaOH solution and extracted three times with 60 mL of MDC. The combined MDC layers were washed with brine, dried over sodium sulphate and distilled under vacuum (crude weight=8 g). The crude mass obtained was dissolved with 10 mL of MDC, and to this 4.5 g benzene sulphonic acid (BSA) dissolved in 30 mL isopropyl acetate (IPAc) was added dropwise over a period of 30 minutes with stirring at RT. The RM was stirred for 30 minutes at RT. The solid obtained was filtered and washed with IPAc and dried under vacuum, resulting in 5 g of the titled compound (Yield=49.5%).

Scheme 3:

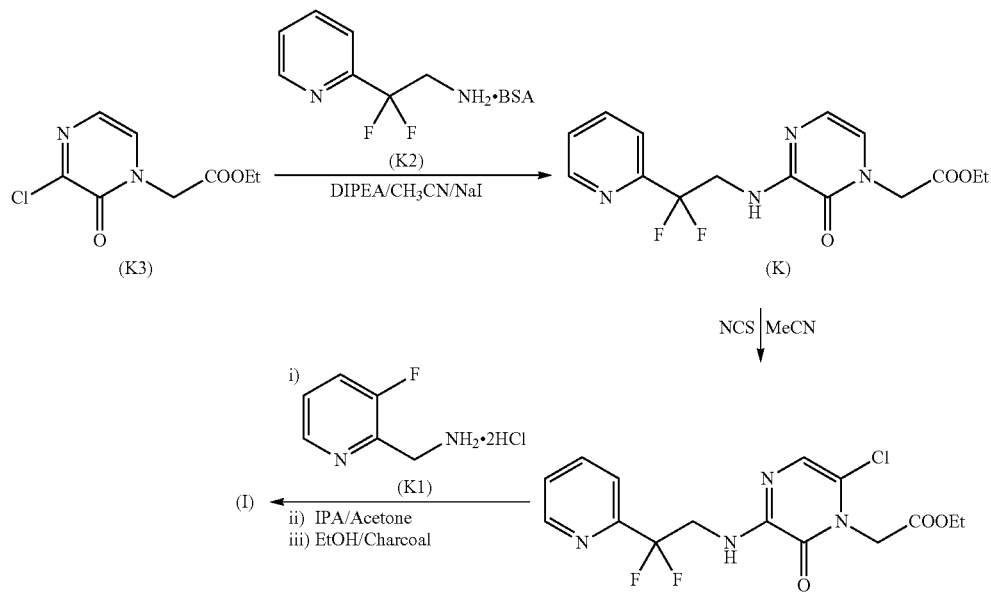

Preparation of 3-fluoro-2-pyridyl-methyl-3-(2,2-difluoro-2-(2-pyridyl)ethylamino -6-chloro-pyrazin-2-one-1-acetamide (I):

Ethyl 3-chloropyrazin(1H)-2-one-1-acetate (K3) was reacted with 2,2-difluoro-2-(2-pyridyl)ethylamine or its salt (K2), which on chlorination and further treatment with 2-aminomethyl-3-fluoropyridine or its salt (K1) by following the procedure, which is illustrated in the art to yield the compound of formula (I). The compound of formula (I) was purified by following the procedure as described below.

EXAMPLE 3

Process for Purifying the Compound of Formula (I)

To the crude sample obtained (10 g), a mixture of 40 mL of acetone and 60 mL of isopropyl alcohol were added, and then the reaction mixture was heated to reflux over a period of 1.5 hours to 2.5 hours. The reaction mixture was filtered and washed with 30 mL of cold isopropyl alcohol (0-5° C.). The product obtained was dried under vacuum at 50-55° C. up to 8-10 hours to yield 8-9 g of the pure compound of formula (I). Yield=80-90%.

Having thus described in detail preferred embodiments of the present invention, it is to be understood that the invention defined by the above paragraphs is not to be limited to particular details set forth in the above description, as many apparent variations thereof are possible without departing from the spirit or scope of the present invention.

We claim:
1. In a process for the preparation of a compound of formula (I):

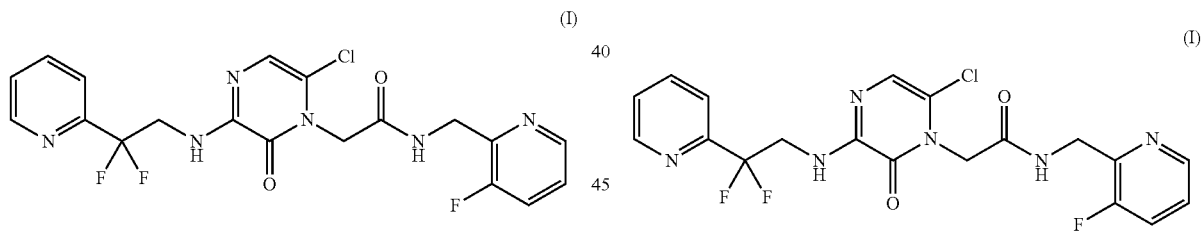

wherein 2,2-difluoro-2-(2-pyridyl)ethylamine or its salt is reacted with ethyl 3-chloropyrazin(1H)-2-one-1-acetate to form ethyl 3 -(2,2-difluoro-2-(2-pyridyl)ethylamino)-pyrazin(1H)-2-one- 1-acetate, which is chlorinated to form:

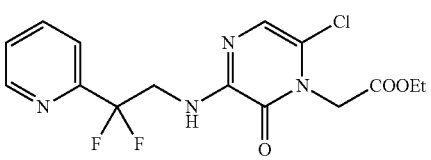 [SMILES: CCOC(=O)Cn1c(Cl)cnc(NCC(F)(F)c2ccccn2)c1=O]

which is further reacted with 2-aminomethyl-3-fluoropyridine or its salt to form 3-fluoro-2-pyridylmethyl-3 -(2, 2-difluoro-2-(2-pyridyl)ethylamino)-6-chloropyrazin-2-one- 1 -acetamide, the compound of formula (I), the improvement comprising:

reducing 2-cyano-3-fluoropyridine with Raney Nickel in the presence of an acid to form 2-aminomethyl-3-fluoropyridine or its salt;

reacting 2,2-difluoro-2-pyridin-2-ylethanol with 4-toluenesulfonyl chloride to form 2,2-difluoro-2-pyridin-2-ylethyl 4-methylbenzenesulfonate, which is converted to 2,2-difluoro-2-(2-pyridyl)ethylamine or its salt by reacting with ammonia; and optionally purifying the compound of formula (I) by addition of an organic solvent.

2. The process of claim 1, wherein the salt of 2-aminomethyl-3-fluoropyridine or 2,2-difluoro-2-(2-pyridyl)ethylamine_ comprises one or more selected from the group consisting of a hydrochloride, hydrobromide and benzenesulphonate.

3. The process of claim 1, wherein the acid used in reducing 2-cyano-3-fluoropyridine comprises acetic acid or trifluoroacetic acid.

4. The process of claim 1, wherein the organic solvent is selected from the group consisting of a ketone, alcohol, ester, ether, hydrocarbon, halogenated solvent and a mixture thereof.

5. The process of claim 4, wherein the ketone is acetone or butanone.

6. The process of claim 4, wherein the alcohol is selected from the group consisting of methanol, ethanol, n-propanol, isopropanol (IPA), n-butanol, t-butanol, hexanol and isoamyl alcohol.

7. The process of claim 4, wherein the ester is selected from the group consisting of ethyl acetate, methyl acetate and isopropyl acetate.

8. The process of claim 4, wherein the ether is diisopropyl ether or methyl t-butyl ether (MTBE).

9. The process of claim 4, wherein the hydrocarbon is selected from the group consisting of hexane, heptane, cyclohexane, decalin and pentane.

10. The process of claim 4, wherein the halogenated solvent is dichloromethane (MDC) or 1,2-dichloroethane.

11. The process of claim 4, wherein the organic solvent is acetone, isopropyl alcohol or a mixture thereof.

12. The compound 2,2-difluoro-2-pyridin-2-ylethyl 4-methylbenzenesulfonate.

13. A process for the preparation of 2,2-difluoro-2-pyridin-2-ylethyl 4-methylbenzenesulfonate, comprising reacting 2,2-difluoro-2-pyridin-2-ylethanol with 4-toluenesulfonyl chloride.

* * * * *